(12) United States Patent
McKiernan et al.

(10) Patent No.: US 9,757,491 B2
(45) Date of Patent: Sep. 12, 2017

(54) ABSORBENT STRUCTURE COMPRISING AN OIL-SCAVENGER COMPONENT

(75) Inventors: Robin Lynn McKiernan, Mason, OH (US); Axel Meyer, Schwalbach (DE); Gabriele Stiehl, Bad Soden (DE); Carolyn Ann Spitzmueller, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 563 days.

(21) Appl. No.: 13/537,088

(22) Filed: Jun. 29, 2012

(65) Prior Publication Data
US 2013/0006205 A1    Jan. 3, 2013

Related U.S. Application Data

(60) Provisional application No. 61/503,145, filed on Jun. 30, 2011.

(51) Int. Cl.
| | | |
|---|---|---|
| *A61F 13/53* | (2006.01) | |
| *A61L 15/20* | (2006.01) | |
| *A61L 15/18* | (2006.01) | |
| *A61L 15/58* | (2006.01) | |
| *A61L 15/60* | (2006.01) | |

(52) U.S. Cl.
CPC .............. *A61L 15/20* (2013.01); *A61L 15/18* (2013.01); *A61L 15/58* (2013.01); *A61L 15/60* (2013.01)

(58) Field of Classification Search
CPC .......... A61F 13/53; A61F 2013/530481; A61F 2013/530489; A61F 2013/530591; A61F 2013/530671; A61L 15/16; A61L 15/20; A61L 15/34; A61L 15/46; A61L 15/48

USPC .................................................. 604/366–370
See application file for complete search history.

(56) References Cited

U.S. PATENT DOCUMENTS

| | | |
|---|---|---|
| 3,860,003 A | 1/1975 | Buell |
| 4,072,735 A | 2/1978 | Ardemagni |
| 4,168,258 A | 9/1979 | Brauer et al. |
| 4,231,986 A | 11/1980 | Brauer et al. |
| 4,281,210 A | 7/1981 | Brauer et al. |
| 4,666,983 A | 5/1987 | Tsubakimoto et al. |
| 4,695,278 A | 9/1987 | Lawson |

(Continued)

FOREIGN PATENT DOCUMENTS

| | | |
|---|---|---|
| CN | 200992530 | 12/2007 |
| DE | 10204937 A1 | 8/2003 |

(Continued)

OTHER PUBLICATIONS

International Search Report, PCT/US2012/044847, mailed Sep. 14, 2012, 11 pages.

(Continued)

*Primary Examiner* — Kathryn E Ditmer
(74) *Attorney, Agent, or Firm* — Kathleen Y. Carter; James T. Fondriest (57) ABSTRACT

An absorbent structure comprising absorbent polymer particles supported by a substrate layer and immobilized on this substrate layer by a thermoplastic adhesive material and further comprising a component sorbing oily substances that may migrate from the thermoplastic adhesive material is disclosed. The absorbent structure can be suitably incorporated in a disposable absorbent article.

14 Claims, 4 Drawing Sheets

(56) References Cited

U.S. PATENT DOCUMENTS

| | | | |
|---|---|---|---|
| 4,795,454 A | 1/1989 | Dragoo | |
| 4,808,178 A | 2/1989 | Aziz et al. | |
| 4,909,803 A | 3/1990 | Aziz et al. | |
| 4,919,934 A * | 4/1990 | Deckner | A61K 8/0229 424/401 |
| 5,387,207 A | 2/1995 | Dyer et al. | |
| 5,409,771 A | 4/1995 | Dahmen et al. | |
| 5,650,222 A | 7/1997 | DesMarais et al. | |
| 5,681,878 A * | 10/1997 | Klotzsche | A61L 15/26 524/269 |
| 5,834,577 A | 11/1998 | Sojka | |
| 5,837,789 A | 11/1998 | Stockhausen et al. | |
| 6,074,732 A | 6/2000 | Garnier et al. | |
| 6,143,821 A | 11/2000 | Houben | |
| 6,239,228 B1 | 5/2001 | Zajaczkowski et al. | |
| 6,369,121 B1 | 4/2002 | Catalfamo et al. | |
| 6,372,953 B1 | 4/2002 | Young et al. | |
| 6,472,478 B1 | 10/2002 | Funk et al. | |
| 6,503,979 B1 | 1/2003 | Funk et al. | |
| 6,559,239 B1 | 5/2003 | Riegel et al. | |
| 6,657,015 B1 | 12/2003 | Riegel et al. | |
| 6,821,629 B2 | 11/2004 | Garnier et al. | |
| 7,115,276 B1 | 10/2006 | Fischer et al. | |
| 2004/0096408 A1 * | 5/2004 | Elliott | A61K 8/02 424/65 |
| 2004/0175343 A1 | 9/2004 | Osborne et al. | |
| 2004/0231065 A1 | 11/2004 | Daniel et al. | |
| 2004/0241475 A1 | 12/2004 | Morabito | |
| 2005/0165208 A1 | 7/2005 | Popp et al. | |
| 2005/0176910 A1 | 8/2005 | Jaworek et al. | |
| 2005/0215752 A1 | 9/2005 | Popp et al. | |
| 2006/0045890 A1 | 3/2006 | Gonzalez et al. | |
| 2006/0155057 A1 | 7/2006 | Hermeling et al. | |
| 2006/0167215 A1 | 7/2006 | Hermeling et al. | |
| 2006/0211828 A1 | 9/2006 | Daniel et al. | |
| 2006/0251893 A1 | 11/2006 | Boulos et al. | |
| 2007/0043191 A1 | 2/2007 | Hermeling et al. | |
| 2007/0116662 A1 * | 5/2007 | Zielinski | A61K 8/8111 424/70.16 |
| 2007/0207940 A1 * | 9/2007 | Fenyvesi | A61Q 5/02 510/276 |
| 2009/0043273 A1 * | 2/2009 | Carlucci | A61F 13/5323 604/370 |
| 2009/0118689 A1 | 5/2009 | Lawson et al. | |
| 2009/0260754 A1 | 10/2009 | Poel | |
| 2009/0314717 A1 | 12/2009 | Fujieda et al. | |
| 2009/0318884 A1 * | 12/2009 | Meyer et al. | 604/366 |
| 2010/0003312 A1 | 1/2010 | Kanebako et al. | |
| 2010/0036342 A1 | 2/2010 | Carlucci et al. | |
| 2010/0254926 A1 * | 10/2010 | Chappell | A61K 8/0229 424/65 |
| 2010/0330238 A1 | 12/2010 | Wintermantel et al. | |
| 2011/0004241 A1 | 1/2011 | Wintermantel et al. | |
| 2011/0114881 A1 | 5/2011 | Torii et al. | |
| 2012/0258853 A1 * | 10/2012 | Veeraraghavan et al. | 502/62 |

FOREIGN PATENT DOCUMENTS

| | | | |
|---|---|---|---|
| DE | 102007004298 | 7/2008 | |
| EP | 0083022 A2 | 7/1983 | |
| EP | 0368102 | 5/1990 | |
| EP | 0368141 | 5/1990 | |
| EP | 0368141 A2 * | 5/1990 | A61L 15/585 |
| EP | 0530438 | 3/1993 | |
| EP | 0547847 | 6/1993 | |
| EP | 0559476 | 9/1993 | |
| EP | 0632068 | 1/1995 | |
| EP | 0937736 | 8/1999 | |
| EP | 1199327 | 4/2002 | |
| EP | 1447067 | 8/2004 | |
| EP | 1621167 | 2/2006 | |
| JP | 2003026865 | 1/2003 | |
| JP | 2009280790 | 12/2009 | |
| WO | WO 90/15830 A1 | 12/1990 | |
| WO | WO 93/21237 | 10/1993 | |
| WO | WO 94/06387 | 3/1994 | |
| WO | WO 94/24977 | 11/1994 | |
| WO | WO 96/08369 | 3/1996 | |
| WO | WO 97/37757 | 10/1997 | |
| WO | WO 99/45878 A1 | 9/1999 | |
| WO | WO 99/47092 | 9/1999 | |
| WO | WO 01/26700 | 4/2001 | |
| WO | WO 03/015726 | 2/2003 | |
| WO | WO 2007/046052 | 4/2007 | |
| WO | WO 2007/047598 | 4/2007 | |
| WO | WO 2007/123338 | 11/2007 | |
| WO | WO 2009/020910 | 2/2009 | |
| WO | WO 2009/145778 | 12/2009 | |
| WO | WO 2009/155264 A2 | 12/2009 | |
| WO | WO 2009/155265 A2 | 12/2009 | |
| WO | WO 2012/025445 A1 | 3/2012 | |

OTHER PUBLICATIONS

Graziano, Louis C., "New Advances in High Performance Water Based Pressure Sensitive Adhesives", , Book 2, 1985, pp. 469-475.

Graziano, Louis C., "Development of Acrylic Latex Pressure Sensitive Adhesive for Plasticized PVC Films", Journal of Plastic Film and Sheeting, vol. 2, Issue 2, Apr. 1986, pp. 95-110.

Reynolds, J.G., "Hydrophobid Aerogels for Oil-Spill Cleanup—Intrinsic Absorbing Properties", Energy Sources, vol. 23, Issue 9, Nov. 2001, pp. 831-843.

* cited by examiner

ABSORBENT STRUCTURE COMPRISING AN OIL-SCAVENGER COMPONENT

CROSS REFERENCE TO RELATED APPLICATION

This application claims the benefit of U.S. Provisional Application Ser. No. 61/503,145, filed Jun. 30, 2011, which is herein incorporated by reference in its entirety.

FIELD OF THE INVENTION

The present invention relates to an absorbent structure for disposable absorbent articles, for example diapers and the like.

BACKGROUND OF THE INVENTION

Disposable absorbent articles for receiving and retaining bodily discharges such as urine, feces or menses are well known in the art. Examples of these include disposable diapers, training pants, adult incontinence articles and sanitary napkins.

An important component of disposable absorbent articles is the absorbent core structure. The absorbent core structure typically includes absorbent polymer material, such as hydrogel-forming polymer material, also referred to as absorbent gelling material, AGM, or super-absorbent polymer, SAP. This absorbent polymer material ensures that large amounts of bodily fluids, e.g. urine or menses, can be absorbed by the absorbent article during its use and be locked away, thus providing low rewet and good skin dryness.

Traditionally, the absorbent polymer material is incorporated into the absorbent core structure with cellulose or cellulosic fibres. However, over the past years, significant effort has been spent to make thinner absorbent core structures which can still acquire and store large quantities of discharged body fluids, in particular urine. Hereto, it has been proposed to reduce or eliminate these cellulose fibres from the absorbent core structures. To maintain the mechanical stability of the absorbent core structures, small quantities of thermoplastic adhesive material, such as fibrous thermoplastic adhesive material, are added to stabilize the absorbent polymer material. Thus, absorbent structures having the required permeability/porosity, reduced gel-blocking, and that form stable structures in use or transport are provided.

However, during the course of these developments, it has been observed that in some instances, such as after extended storage periods or storages at high temperature, the absorption speed may be reduced when the absorbent polymer material is incorporated into absorbent structures with certain thermoplastic adhesive materials. The inventors found that this may be due to the interactions of certain components of the adhesive thermoplastic material with the surface of the absorbent polymer material. Thermoplastic adhesive materials typically comprise one or more thermoplastic polymer in combination with other thermoplastic diluents, such as tackifying resins, plasticizers and other additives such as antioxidant. Plasticizers are typically compounds of low molecular weight (<2000 g/mole) including mineral oils or organic oils, all together referred herein as "oily substances". Examples of mineral oils include paraffinic oils, naphthenic oils and aromatic oils. The inventors found that with time and/or temperature, these oily substances may tend to partially separate from the thermoplastic adhesive material and migrate through the absorbent structure in the direction of the absorbent polymer material, thus rendering the surface of the absorbent polymer material more hydrophobic, and thereby reducing the affinity of the surface with hydrophilic materials such as urine, thereby leading to an overall loss of performance. The loss of performance resulting from the migration of some of the components of the thermoplastic adhesive material may be compensated by the addition of more absorbent polymer materials which is particularly costly.

Therefore, there is still a need to overcome the negative impact that separation and migration of some components of the thermoplastic adhesive material may have on the performances of the absorbent structure in order to provide absorbent structures/absorbent articles which perform satisfactory when thermoplastic adhesive material is added to the absorbent polymer material.

SUMMARY OF THE INVENTION

The present invention is dedicated to an absorbent structure for use in disposable absorbent articles which comprises:
 (a) a substrate layer,
 (b) absorbent polymer particles supported by said substrate layer,
 (c) a thermoplastic adhesive material comprising one or more oily substances, said thermoplastic adhesive material immobilizing said absorbent polymer particles on said substrate layer,
 (d) an oil-scavenger component contacting said absorbent polymer particles and said thermoplastic adhesive material.

The present invention is also dedicated to a process for manufacturing such an absorbent structure and to a disposable absorbent structure comprising such an absorbent structure.

DETAILED DESCRIPTION OF THE INVENTION

As used herein "absorbent article" refers to devices which are intended to be placed against the skin of a wearer to absorb and contain the various exudates discharged from the body. Examples of absorbent articles include incontinence articles such as diapers (infant or adult diapers, pant-like diapers such as training pants), diaper holders or incontinence pads. Further examples of absorbent articles are feminine hygiene products such as sanitary napkins and panty-liners. In a preferred embodiment of the present invention, the absorbent articles are diapers, sanitary napkins and panty-liners.

"Disposable" is used herein to describe articles that are generally not intended to be laundered or otherwise restored or reused (i.e., they are intended to be discarded after a single use and, may be recycled, composted or otherwise disposed of in an environmentally compatible manner).

As used herein "absorbent structure" refers to a three dimensional structure useful to absorb and contain liquids, such as urine, menses or blood. The absorbent structure may be the absorbent core of an absorbent article or may be part of the absorbent core of an absorbent article, i.e. an absorbent component of the absorbent core, as will be further described herein.

As used herein "absorbent core" refers to a component of an absorbent article typically disposed between a topsheet and backsheet of an absorbent article. The absorbent core of an absorbent article may comprise one or more absorbent structures and optionally further layers, such as for instance a cover layer.

"Absorbent polymer particles" as used herein refers to substantially water-insoluble polymer particles that can absorb at least 5 times their weight of a 0.9% saline solution in de-mineralized water as measured using the Centrifuge Retention Capacity test (Edana 441.2-01).

"Elastomeric" and "elastic" as used herein refers to a material that will exhibit stress induced deformation that is partially or completely reversed upon removal of the stress.

"Oily substances" as used herein refers to mineral oils or organic oils, including paraffinic oils, naphthenic oils and aromatic oils.

In the following description of the invention, the surface of an absorbent article, or of an element thereof, which faces in use in the direction of the wearer, is called the "wearer-facing surface". Conversely, the surface facing in use in the direction of the garment is called the "garment-facing surface". The absorbent article, as well as any element thereof, such as, for example the absorbent structure, has therefore a wearer-facing surface and a garment-facing surface.

Absorbent Structure

The absorbent structure comprises absorbent polymer particles, and optionally cellulose, supported by a substrate layer and immobilized on said substrate layer by a thermoplastic adhesive material comprising oily substances. The absorbent structure further comprises an oil-scavenger component. An "oil-scavenger" component as used herein refers to a component, or a mixture thereof, that sorbs oily substances, e.g. mineral or organic oils. The addition of such a component to the absorbent structure reduces the above-mentioned negative effects associated with the separation and migration of the oily substances contained in the thermoplastic adhesive material.

The absorbent structure typically comprises less than 5% by weight of cellulose, more typically less than 2% and most typically is cellulose free. "Cellulose" as used herein refers to comminuted wood pulp in the form of fibers, typically also referred to in the art as "air-felt". The resulting absorbent structures have a reduced thickness in the dry state compared to conventional absorbent structure comprising cellulosic fibers. The reduced thickness helps to improve the fit and comfort of the absorbent article for the wearer.

The absorbent structure may comprise a weight ratio of the absorbent polymer particles to the oil-scavenger component of from 2:1 to 1000:1, or from 3:1 to 350:1, or from 4:1 to 200:1 or from 4:1 to 99:1.

Oil-Scavenger Component(s)

Suitable oil-scavenger components are effective at sorbing oily substances, such as mineral or organic oils. Particularly when used in an absorbent structure, suitable oil-scavenger components are effective at sorbing oily substances whilst preventing hydrophobization of the absorbent polymer particles supported by the substrate layer. Indeed, the affinity of the absorbent polymer particles for hydrophilic materials to be absorbed, such as urine, should not be negatively affected by the addition of the oil-scavenger component to the absorbent structure, i.e. the absorbent polymer particles should not repel urine. Resultantly, the ratio ($AI_{oilscavenger}/AI_{control}$) is greater than or equal to 1 (as measured according to the Absorption Index Test disclosed herein).

The oil-scavenger component is typically in particulate form. The oil-scavenger component is typically provided in particulate form when forming the absorbent structure, i.e. the oil-scavenger is added to, or onto, the absorbent polymer particles at a temperature below its melting point. The oil-scavenger particles may have any shapes including, but not limited to, spherical, spherical-like, cubical, pyramidal, irregular shapes and combinations thereof.

The average oil-scavenger particle size distribution may range from 0.005 µm to 5 mm, or from 0.15 µm to 3 mm, or from 0.2 µm to 2 mm, or from 0.25 µm to 1 mm. The particle size refers to the diameter of a particle (the diameter of an irregular volume is the longest distance between two points on its surface). The particle size distribution can be determined as it is known in the art, for example by means of dry sieve analysis (EDANA 420.02 "Particle Size distribution). The inventors found that it may be beneficial to include partially or exclusively oil-scavenger particles of relatively low size in the absorbent structure, i.e. particle size lower than 1 mm, e.g. from 0.005 µm to 900 µm, or from 0.01 µm to 800 µm or from 0.02 µm to 700 µm as particles of small size have more surface area available and thus can sorb oily substances more quickly, preferably even before the oily substances reach the absorbent polymer particles.

The oil-scavenger component may be a single compound or may be a mixture of compounds.

Suitable oil-scavenger components include non-polymeric organic compounds, organic polymer particles and inorganic mineral materials.

Non-Polymeric Organic Compounds

Examples of non-polymeric organic compounds suitable as oil-scavenger components include compounds selected from the group consisting of aliphatic mono- or dihydric alcohol having at least 12 carbon atoms, aliphatic mono- or dicarboxylic acid having at least 12 carbon atoms and combinations thereof.

Aliphatic mono- or dihydric alcohols having at least 12, or at least 14, or at least 16 carbon atoms and aliphatic mono- or dicarboxylic acids having at least 12, or at least 14, or at least 16 carbon atoms may be linear or branched. In some embodiments, aliphatic mono- or dihydric alcohols and mono- or dicarboxylic acids may have at least 12 carbon atoms and up to 20 carbon atoms.

Typically, compounds belonging to these classes are believed to be suitable as oil-scavenger components as the result of their long aliphatic chain believed to provide affinity for oily substances and of their polar functionalities (i.e. alcohol or acidic function) believed to confer enough hydrophilicity for not repelling hydrophilic compounds, such as urine (i.e. it does not hydrophobize the absorbent polymer particles). Preferred aliphatic mono- or dihydric alcohol and aliphatic mono- or dicarboxylic acid are linear compounds.

Exemplary aliphatic mono- or dihydric alcohols having at least 12 carbon atoms include, but are not limited to, 1-octadecanol, 1,2-dodecanediol, 1,2-hexadecanediol, 1-tetradecanol, 1,2-tetradecanediol, 1,14-tetradecanediol, 1-octadecanol, 1,2-octadecanediol, 1,12-octadecanediol.

Exemplary aliphatic mono- or dicarboxylic acids having at least 12 carbon atoms include, but are not limited to, dodecanoic acid, octadecanoic acid, hexadecanedioic acid, tetradecanoic acid, tetradecanedioic acid.

Organic Polymer Particles

Organic polymer particles suitable as oil-scavenger components include particles produced from high internal phase emulsions (HIPEs). Particles produced from HIPEs are known in the art and can be obtained by polymerizing water-in-oil emulsions, such as described in U.S. Pat. No. 5,387,207, U.S. Pat. No. 5,650,222, U.S. Pat. No. 6,369,121 or WO 99/45878 A1, and WO 99/45878, the contents of which are hereby incorporated by reference. The HIPE is typically obtained as foam and then reduced to particles (e.g. via pulverizing, cutting, chopping, grinding or milling).

A suitable process for obtaining a foam from a High Internal Phase Emulsion is disclosed in WO 99/47092. It comprises the step of providing a first phase, preferably a water phase including a free radical initiator, and providing a second phase, preferably an oil phase. The ratio of the first phase to the second phase is between about 2:1 and about 250:1.

The free radical initiator herein can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfate, L-ascorbic acid or ferrous salts. The free radical initiator is preferably present at up to about 20 mole percent based on the total moles of polymerizable monomers in the oil phase. Preferably, the initiator is present in an amount of from about 0.001 to 10 mole percent based on the total moles of polymerizable monomers in the oil phase.

The oil phase herein comprises (a), preferably from about 80% to about 98% by weight, of polymerizable monomers and (b), preferably from about 2% to about 20% by weight of an emulsifier component or a mixture thereof which is soluble in the oil phase and which is suitable for forming a stable water-in-oil emulsion.

The polymerizable monomers may include methacrylate-based monomers (e.g. methyl methacrylate) and styrene-based monomers (e.g. styrene), various structural isomers (ortho, meta, para substituted) of divinyl benzene as well as of vinyl benzene. Further examples of monomers are disclosed in U.S. Pat. No. 5,387,207, the content of which is hereby incorporated by reference.

Suitable emulsifiers can include any of a number of conventional emulsifiers which are soluble in the oil phase used to form the emulsion. Usually, these emulsifiers are nonionic materials and may have a wide range of HLB values. Examples of some typical emulsifiers include sorbitan esters such as sorbitan laureates (e.g., SPAN® 20), sorbitan palmitates (e.g., SPAN® 40), sorbitan stearates (e.g., SPAN® 60 and SPAN® 65), sorbitan monooleates (e.g., SPAN® 80), sorbitan trioleates (e.g., SPAN® 85), sorbitan sesquioleates (e.g., EMSORB® 2502), and sorbitan isostearates (e.g., CRILL® 6); polyglycerol esters and ethers (e.g., TRIODAN® 20); polyoxyethylene fatty acids, esters and ethers such as polyoxyethylene (2) oleyl ethers, polyethoxylated oleyl alcohols (e.g. BRIJ® 92 and SIMUSOL® 92), etc.; mono-, di-, and triphosphoric esters such as mono-, di-, and triphosphoric esters of oleic acid (e.g., HOSTAPHAT KO3OON), polyoxyethylene sorbitol esters such as polyoxyethylene sorbitol hexastearates (e.g., TLAS® G-1050), ethylene glycol fatty acid esters, glycerol mono-isostearates (e.g., IMWITOR 780K), ethers of glycerol and fatty alcohols (e.g., CREMOPHOR WO/A), esters of polyalcohols, synthetic primary alcohol ethylene oxide condensates (e.g., SYNPERONIC A2), mono and diglycerides of fatty acids (e.g., ATMOS® 300), and the like. Other preferred emulsifiers include the diglycerol esters derived from monooleate, monomyristate, monopalmitate, and monoisostearate acids. Mixtures of these emulsifiers are also particularly useful.

The first and second phases are processed using a static mixer which provides sufficient shear to emulsify the first phase in the second phase to create the high internal phase emulsion (HIPE). The produced HIPE emulsion is heated (preferably to at least about 65° C., more preferably at least about 80° C., most preferably at least about 95° C.) to initiate the free radical polymerization and cured until substantially all of the monomers (at least about 99%) has been converted to polymer. A foam is thus obtained.

The foam obtained through the HIPE is thereafter reduced to particles by any suitable means, preferably via a pulverizing, cutting, chopping, grinding or milling operation. Other suitable means include the use of eroding tools such as a high speed eroding wheel with dust collector wherein the surface of the wheel is engraved with a pattern or is coated with abrasive sandpaper or the like to promote the foam to form the particles. The HIPE foam herein can be ground using commercially available equipment such as the Hosokawa Alpine Grinder.

Alternatively, the foam may be reduced to particles in several stages. First the bulk foam can be broken into pieces of a few cm dimensions by manually chopping or cutting, or using a mechanical tool such as a lumpbreaker, for example the Model 2036 from S Howes, Inc. of Silver Creek, N.Y. In a second stage, the lumps are agitated using a propeller or saw toothed disc dispersing tool, which causes the foam to release entrapped water and form a liquid slurry of polymer particles dispersed in aqueous phase. In a third stage, a high shear mixer (such as the Ultra Turrax rotor stator mixer from IKA Works, Inc., Wilmington, N.C.) can be employed to reduce the particle size of the primary slurry to that required for particles.

Inorganic Mineral Materials

Suitable oil-scavenger compounds include inorganic mineral materials such as silica or sorbent clays. These materials are believed to allow for great oil sorption because of their high surface area (>200 m$^2$/g).

Silica includes amorphous silica with high surface area (>200 m$^2$/g) and ultrafine particle size, i.e. from 5 to 45 nm. These include silica aerogel and fumed silica. The silica is preferably hydrophilic. Examples of suitable hydrophilic fumed silica include, but are not limited to, Aerosil® 150, Aerosil® 200, Aerosil® 300, Aerosil® 380 as available from Evonik, Germany. Fumed silicas are also available from Cabot and Wacher Chemie-Dow Corning. Examples of silica aerogel include Nanogel® Aerogel as available from Cabot Corporation.

Sorbent clays include clay minerals, in particular aluminum silicates such as kaolin, bentonite, Fuller's Earth, shale clay, montmorillonite, kaolinite, vermiculite, smectite, chlorite, illite.

Substrate Layer

The substrate layer of the absorbent structure may be any material capable to support the absorbent polymer particles. Typically, it is a web or sheet material, such as a foam, film, woven and/or nonwoven material.

"Nonwoven material" as used herein refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise two steps: fiber laying onto a forming surface and fiber bonding. The fiber laying step may comprise spunlaying, meltblowing, carding, airlaying, wetlaying, coform and combinations thereof. The fiber bonding step may comprise hydroentanglement, cold calendering, hot calendering, through air thermal bonding, chemical bonding, needle punching, and combinations thereof.

Woven or nonwoven materials may comprise natural fibers or synthetic fibers or combinations thereof. Examples of natural fibers may include cellulosic natural fibers, such as fibers from hardwood sources, softwood sources, or other non-wood plants. The natural fibers may comprise cellulose, starch and combinations thereof. The synthetic fibers can be any material, such as, but not limited to, those selected from the group consisting of polyolefins (polypropylene and polypropylene copolymers, polyethylene and polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture that makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Any or all of the fibers may be treated before, during, or after manufacture to change any desired properties of the fibers.

The nonwoven material may be a laminate. The laminate may comprise spunbond layer(s) (S), and/or meltblown layer(s) (M), and/or carded layer(s) (C). Suitable laminates include, but are not limited to, SS, SSS, SMS or SMMS. The nonwoven material may have a basis weight from about 5 to 100 $g/m^2$, or from about 10 to 40 $g/m^2$, or from about 10 to 30 $g/m^2$.

Absorbent Polymer Particles

Typically the absorbent polymer particles suitable for use in the absorbent structure according to the present invention can comprise any absorbent polymer particles known from superabsorbent literature, for example such as described in Modern Superabsorbent Polymer Technology, F. L. Buchholz, A. T. Graham, Wiley 1998.

The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

The absorbent polymer particles can be selected among polyacrylates and polyacrylate based materials that are internally and/or surface cross-linked, such as for example partially neutralized cross-linked polyacrylates or acid polyacrylate. Examples of absorbent polymer particles suitable in the present invention are described for instance in the PCT Patent Application WO 07/047,598, WO 07/046,052, WO2009/155265 and WO2009/155264.

The absorbent polymer particles are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as crosslinkers described in WO2009/155265.

The absorbent polymer particles may be externally cross-linked (post cross-linked).

Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The absorbent polymer particles may have surface modifications, such as being coated or partially coated with a coating agent. Examples of coated absorbent polymer particles are disclosed in WO2009/155265. The coating agent may be such that it renders the absorbent polymer particles more hydrophilic. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%, or from 0.2% to 1% by weight of the surface-modified absorbent polymer particles.

Typically, the absorbent polymer particles can have a selected particle size distribution. For example, the absorbent polymer particles may have a particle size distribution in the range from 45 µm to 4000 µm, more specifically from 45 µm to about 1000 µm, or from about 100 µm to about 850 µm, or from about 100 µm to about 600 µm. The particle size distribution of a material in particulate form can be determined as it is known in the art, for example by means of dry sieve analysis (EDANA 420.02 "Particle Size distribution). Optical methods, e.g. based on light scattering and image analysis techniques, can also be used.

Typically, the absorbent structure comprises an average amount of absorbent polymer particles per surface area of from 50 to 2200 g/m², or from 100 to 1500 g/m² or even from 200 to 1200 g/m². The amount of absorbent polymer particles may or not vary along the length of the absorbent structure and/or absorbent core. In some embodiments, the absorbent structure is profiled in its longitudinal direction. It has been found that, for most absorbent articles such as diapers, the liquid discharge occurs predominately in the front half of the diaper. The front half of the absorbent core/structure should therefore comprise most of the absorbent capacity of the core/structure. Thus, according to certain embodiments, the front half of said absorbent structure may comprise more than about 60% of the absorbent polymer particles, or more than about 65%, 70%, 75%, 80%, 85%, or 90% of the absorbent polymer particles.

Thermoplastic Adhesive Material

The absorbent structure comprises a thermoplastic material comprising one or more oily substances. As mentioned above, the oily substances are typically organic or mineral oils used as plasticizers in the formulation of the thermoplastic adhesive material. These plasticizers are typically compounds of low molecular weight (<2000 g/mol) with low softening points. The thermoplastic material may serve to at least partially immobilize the absorbent polymer particles on the substrate layer.

Without wishing to be bound by theory, it is believed that those thermoplastic adhesive materials which are most useful for immobilizing the absorbent polymer particles combine good cohesion and good adhesion behavior. Good adhesion may promote good contact between the thermoplastic adhesive material and the absorbent polymer particles and the substrate layer. Good cohesion reduces the likelihood that the adhesive breaks, in particular in response to external forces, and namely in response to strain. When the absorbent structure/core absorbs liquid, the absorbent polymer particles swell and subject the thermoplastic adhesive material to external forces. The thermoplastic adhesive material may allow for such swelling, without breaking and without imparting too many compressive forces, which would restrain the absorbent polymer particles from swelling. Thermoplastic adhesive materials suitable for use in the present invention includes hot melt adhesives comprising at least a thermoplastic polymer in combination with a plasticizer and other thermoplastic diluents such as tackifying resins and additives such as antioxidants. Exemplary suitable hot melt adhesive materials are described in EP 1447067 A1, particularly at sections [0050] to [0063]. In some embodiments, the thermoplastic polymer has typically a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and $(A-B)_n$ radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. The thermoplastic adhesive material, typically a hot-melt adhesive material, is generally present in the form of fibres, i.e. the hot melt adhesive can be fiberized. In some embodiments, the thermoplastic adhesive material forms a fibrous network over the absorbent polymer particles and the oil-scavenger component. Typically, the fibres can have an average thickness from about 1 μm to about 100 μm, or from about 25 μm to about 75 μm, and an average length from about 5 mm to about 50 cm. In particular the layer of hot melt adhesive material can be provided such as to comprise a net-like structure. In certain embodiments the thermoplastic adhesive material is applied at an amount of from 0.5 to 30 g/m², or from 1 to 15 g/m², or from 1 and 10 g/m² or even from 1.5 and 5 g/m² per substrate layer.

In some embodiments, the absorbent structure may also comprise a thermoplastic adhesive material deposited on the substrate before application of the absorbent polymer particles on the substrate layer. The thermoplastic adhesive material deposited on the substrate before application of the absorbent polymer particles may enhance the immobilization of the absorbent polymer particles on the substrate layer. It may comprise the same thermoplastic adhesive material as described hereinabove. An example of commercially available adhesive is H.B. Fuller Co. (St. Paul, Minn.) Product No. HL-1620-B. The thermoplastic adhesive material may be applied to the substrate layer by any suitable means.

A typical parameter for a hot melt adhesive suitable for use in the present invention can be a loss angle tan Delta at 60° C. of below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic adhesive material has a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive material may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or less than 70°, as measurable with ASTM D 5725-99.

The thermoplastic adhesive material may be present at a level of 0.5% to 14%, or from 1.0% to 10%, or from 2% to 5% by weight of the absorbent structure.

The thermoplastic adhesive material may be present in the absorbent structure such that the weight ratio of the absorbent polymer particles to the thermoplastic adhesive material is from 1:1 to 50:1, or from 2:1 to 40:1, or from 3:1 to 25:1, or from 3:1 to 15:1.

Absorbent Structures and Processes for Making Thereof

As disclosed above, the absorbent structure of the present invention comprises an oil-scavenger component. The oil-scavenger component is disposed within the absorbent structure such that at least part of the oil-scavenger component contacts both the absorbent polymer particles and the thermoplastic adhesive material. The oil-scavenger component may be mixed with the absorbent polymer particles or dusted on the surface of absorbent polymer particles and the resulting particles are then deposited on the substrate layer. Alternatively, the oil-scavenger component may be deposited on the surface of the absorbent polymer particles after deposition of the absorbent polymer particles on the substrate layer. The oil-scavenger is preferably in a particulate form.

The absorbent polymer particles, and optionally cellulose when present, may be distributed on the substrate layer such as to form as a continuous layer, i.e. an uninterrupted layer of absorbent polymeric particles and cellulose when present. Alternatively, the absorbent polymer particles, and optionally cellulose when present, may be distributed on the substrate layer such as to form a discontinuous layer. In these embodiments, the absorbent polymer particle and cellulose when present, may be deposited on the substrate layer in clusters of particles (and cellulose when present), thus forming a discontinuous layer or an interrupted layer of absorbent polymer particles (and cellulose when present). The clusters of absorbent polymer particles (and cellulose when present) may have a variety of shape including, but not limited to, circular, oval, square, rectangular, triangular and the like. Suitable methods for depositing particles in cluster of particles are disclosed in EP 1621167 A2, EP 1913914 A2 and EP 2238953 A2. In these embodiments, the oil-scavenger component may be mixed with the absorbent polymer particles or dusted on the surface of absorbent polymer particles prior to their deposition on the substrate layer or the oil-scavenger component may be deposited on the surface of the absorbent polymer particles after deposition of the absorbent polymer particles on the substrate layer.

Figure 1:
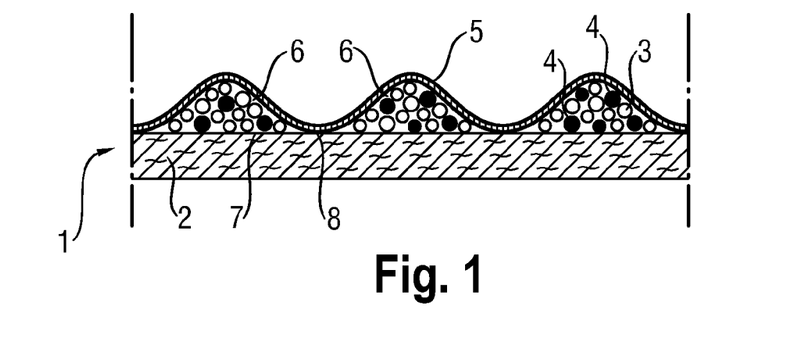
FIG. 1 is a schematic cross-section of an absorbent structure according to one embodiment of the present invention.

In one embodiment, such as illustrated in FIG. 1, the absorbent structure 1 comprises a substrate layer 2, a mixture of absorbent polymer particles 3 and oil-scavenger particles 4 deposited on the substrate layer 2 in clusters of particles and a thermoplastic adhesive material 5 deposited on the mixture of absorbent polymer particles 3 and oil-scavenger particles 4. The thermoplastic adhesive material 5 holds and immobilizes the mixture of absorbent polymer particles 3 and oil-scavenger particles 4 on the substrate layer 2. The thermoplastic adhesive material, although not represented in the figure, may penetrate into the clusters of absorbent polymer particles and oil-scavenger particles and into the substrate layer, thus providing further immobilization and affixation. The thermoplastic adhesive material may be applied as a continuous layer over the mixture of absorbent polymer particles and oil-scavenger particles such as to contact at least partially the mixture of particles and partially the substrate layer, i.e. the thermoplastic adhesive material is laid down onto the discontinuous layer of absorbent polymer particles and oil-scavenger particles such that the thermoplastic adhesive material is in direct contact with the particles and in direct contact with the substrate layer where the substrate layer is not covered by particles. Typically, the thermoplastic adhesive material is applied as a fibrous layer which is at least partially in contact with the mixture of particles and partially in contact with the substrate layer. When present in the form of fibers, the thermoplastic adhesive material forms a fibrous network that immobilizes the mixture of absorbent polymer particles and oil-scavenger particles on the substrate layer. The absorbent structure may comprise a further thermoplastic adhesive material (not shown in the figure) deposited on the substrate layer before the deposit of the mixture of absorbent polymer particles and oil-scavenger particles. Typically, the mixture of absorbent polymer particles and oil-scavenger particles are deposited on the substrate layer in clusters 6 of particles, i.e. as a discontinuous layer which comprises land areas 7 and junction areas 8 between the land areas 7. As used herein, "land areas" refers to areas where the subsequently applied thermoplastic adhesive material does not contact the substrate layer directly and "junction areas" refers to areas where the subsequently applied thermoplastic adhesive material does contact the substrate layer directly. The junction areas contain little or no absorbent polymer particles. Mixture of absorbent polymer particles and oil-scavenger particles may be preferred when the particles are of about the same size. Alternatively, in embodiments where the oil-scavenger particles size is smaller than absorbent polymer particles size, the oil-scavenger particles may be dusted on the surface of the absorbent polymer particles prior to their deposition on the substrate layer.

Figure 2:
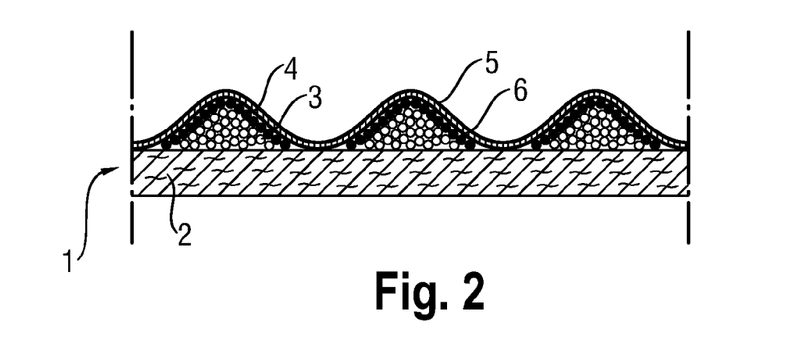
FIG. 2 is a schematic cross-section of an absorbent structure according to one embodiment of the present invention.

In one embodiment, such as illustrated in FIG. 2, the absorbent structure 1 comprises a substrate layer 2, absorbent polymer particles 3 deposited on the substrate layer 2 in clusters of particles, oil-scavenger particles 4 deposited on said absorbent polymer particles 3 and a thermoplastic adhesive material 5 deposited on the oil-scavenger particles 4. The thermoplastic adhesive material 5 holds and immobilizes the absorbent polymer particles 3 and the oil-scavenger particles 4 on the substrate layer 2. The thermoplastic adhesive material, although not represented in the figure, may penetrate into the clusters of absorbent polymer particles and oil-scavenger particles and into the substrate layer, thus providing further immobilization and affixation. The oil-scavenger particles may be deposited on the absorbent polymer particles by any suitable means. Preferably, the oil-scavenger particles are deposited exclusively on the absorbent polymer particles. The thermoplastic adhesive material may be applied as disclosed above so as to immobilize the oil-scavenger particles and the absorbent polymer particles on the substrate layer. The absorbent polymer particles are deposited on the substrate layer in clusters 6 of particles, i.e. as a discontinuous layer, as disclosed above. The absorbent structure may comprise a further thermoplastic adhesive material (not shown in the figure) deposited on the substrate layer before the deposit of the absorbent polymer particles. This further thermoplastic adhesive material may be deposited as disclosed above. In such an embodiment, oil-scavenger particles may be deposited on the further thermoplastic adhesive material prior to the deposit of the absorbent polymer particles. Preferably, the oil-scavenger particles are deposited such as to be exclusively located underneath the absorbent polymer particles.

The absorbent structure according to the present invention may be manufactured according to a process comprising the steps of providing a substrate layer, providing absorbent polymer particles, providing a thermoplastic adhesive material, providing an oil-scavenger component in particulate form. The subsequent steps of the process may then vary depending on the desired final absorbent structure.

In one embodiment, the process may further comprise the subsequent steps of mixing the oil-scavenger particles and the absorbent polymer particles, depositing the mixture of oil-scavenger particles and absorbent polymer particles on the substrate layer and depositing the thermoplastic adhesive material on the mixture of oil-scavenger particles and absorbent polymer particles. Preferably, the oil-scavenger particles and the absorbent polymer particles are mixed when the oil-scavenger particles and absorbent polymer particles have about the same particle size. FIG. 1 is representative of an absorbent structure made according to said process.

In one alternative embodiment, the process may further comprise the subsequent steps of dusting the oil-scavenger particles on the surface of the absorbent polymer particles, depositing the absorbent polymer particles on the substrate layer and depositing the thermoplastic adhesive material on the absorbent polymer particles.

In one alternative embodiment, the process may further comprise the subsequent steps of depositing the absorbent polymer particles on the substrate layer, depositing the oil-scavenger particles on the absorbent polymer particles and depositing the thermoplastic adhesive material on the oil-scavenger particles. FIG. 2 is representative of an absorbent structure made according to said process.

In any of the disclosed processes, a further thermoplastic adhesive material may be deposited on the substrate layer prior to the deposition of the absorbent polymer particles. The further thermoplastic adhesive material may be the same or may be different from the thermoplastic adhesive material described above. Suitably, oil-scavenger particles may be partially contacting said further thermoplastic adhesive material, i.e. oil-scavenger particles may be deposited on the further thermoplastic adhesive material.

In an alternative embodiment, the oil-scavenger component may be added to the thermoplastic adhesive material and the combination oil-scavenger component/thermoplastic adhesive material is then deposited on the absorbent polymer particles.

The absorbent structure disclosed herein may be absorbent core of an absorbent article or may be part of the absorbent core.

In some embodiments, the absorbent structure may further comprise a cover layer on the thermoplastic adhesive material to provide the absorbent core of an absorbent article. The cover layer may be a separate sheet or web or it may be unitary with the substrate layer. In such a case, the substrate layer supporting the absorbent polymer particles is folded to form a top and bottom layer which encloses the absorbent polymer particles. The cover layer may be provided of the same material as the substrate layer, or may be provided of a different material. The layers may be bonded together at about the periphery to enclose the absorbent polymer particles therein, e.g. by adhesive bonding and/or heat bonding.

In some embodiments, the absorbent core of an absorbent article may comprise two or more absorbent structures as disclosed herein which are combined or superposed.

Figure 3:
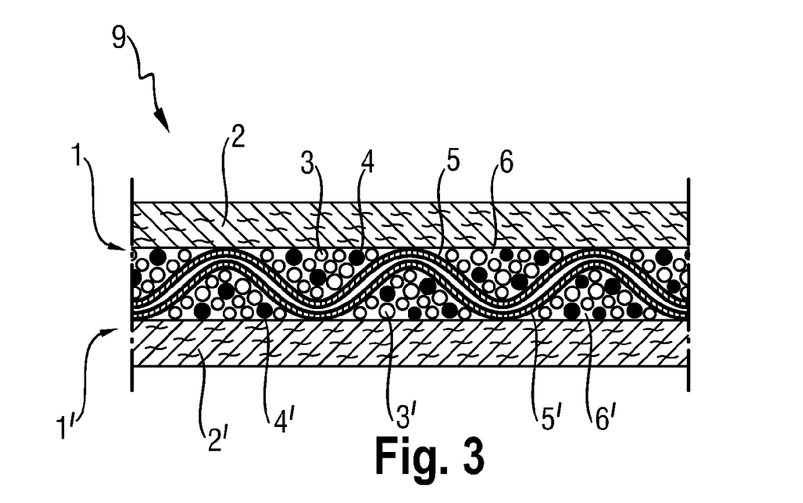
FIG. 3 is a schematic cross-section of an absorbent core according to one embodiment of the present invention.

FIG. 3 illustrates one such embodiment wherein two absorbent structures 1 and 1' are combined to form an absorbent core 9. The first absorbent structure 1 of the absorbent core 9 comprises a substrate layer 2, a mixture of absorbent polymer particles 3 and oil-scavenger particles 4 deposited on the substrate layer, and a layer of thermoplastic adhesive material 5 applied on the mixture of absorbent polymer particles 3 and oil-scavenger particles 4. Although not illustrated, the first absorbent structure 1 may also include a cover layer. Likewise, the second absorbent structure 1' of the absorbent core 9 comprises a substrate layer 2', a mixture of absorbent polymer particles 3' and oil-scavenger particles 4' deposited on the substrate layer 2' and a layer of thermoplastic adhesive material 5' on the mixture of absorbent polymer particles 3' and oil-scavenger particles 4'. Although not illustrated, the second absorbent structure 1' may also include a cover layer. The first and second absorbent structure 1 and 1' are combined together to form the absorbent core 9. The absorbent structures 1 and 1' may be offset such that the clusters 6 of absorbent polymer particles 3 on the substrate layer 2 register with the clusters 6' of absorbent polymer particles 3' on the substrate layer 2'. When the clusters are appropriately sized and arranged, the resulting combination of absorbent polymer particles is a substantially continuous layer of absorbent polymer particles across the absorbent polymer particles area of the absorbent core (i.e. first and second substrate layers do not form a plurality of pockets, each containing a cluster of absorbent polymer particles therebetween).

Disposable Absorbent Articles Comprising the Absorbent Structure

As mentioned above, the absorbent structure of the present invention may constitute the absorbent core of a disposable absorbent article or may be part thereof. The absorbent core may be then suitably incorporated in a disposable absorbent article, e.g. diapers (infant or adult diapers, pant-like diapers such as training pants), diaper holders, incontinence pads, sanitary napkins and panty-liners. Generally, the absorbent core is disposed between the topsheet and the backsheet of an absorbent article.

Figure 4:
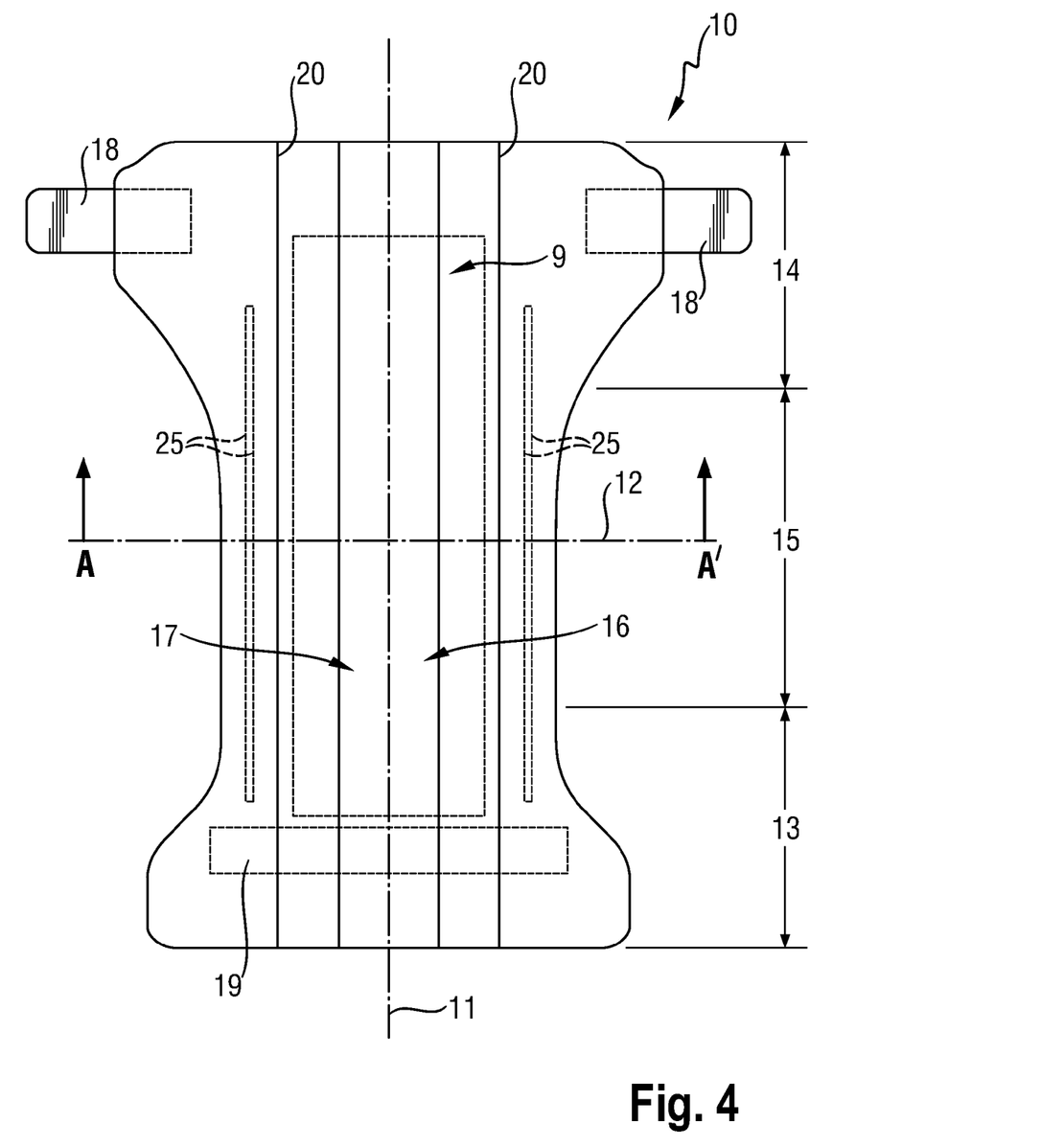
FIG. 4 is a plan view of a diaper.

FIG. 4 illustrates a diaper as one embodiment of an absorbent article. However, as the skilled person is aware of, most of the components and materials described herein below are also applicable to other disposable absorbent articles.

The diaper 10 has a longitudinal axis 11 and a transverse axis 12. The diaper has further an inner, body facing surface and an outer, garment facing surface opposed to the inner surface. One end portion of the diaper is configured as a front waist region 13 (which is the front one third of the article, having one third of the length of the article). The opposite end portion is configured as a back waist region 14 (back one third) of the diaper, having one third of the length of the article. An intermediate portion of the diaper is configured as a crotch region 15 (centre one third), which extends longitudinally between the front and back waist regions, also having one third of the length of the article. The crotch region is that portion of the diaper which, when the diaper is worn, is generally positioned between the wearer's legs. The chassis 16 of the diaper comprises typically a topsheet 17, which may be liquid pervious. The topsheet may be at least partially hydrophilic. So-called apertured topsheets may also be used. Topsheets with one or more (large) openings may also be used. The topsheet may also include a skin care composition, e.g., a lotion.

The chassis 16 typically also comprises a backsheet (not shown in FIG. 1). The backsheet may be vapor pervious but liquid impervious. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet can also allow the transfer of at least water vapor, or both water vapor and air through it.

The chassis further 16 includes an absorbent core 9 disposed between the topsheet 17 and the backsheet of the absorbent article. The configuration and construction of the absorbent core may vary, e.g. the absorbent core may have varying caliper zones, a hydrophilic gradient, a superabsorbent gradient, or lower average density and lower average basis weight acquisition zones. The total absorbent capacity of the absorbent core should, however, be compatible with the design loading and the intended use of the diaper. Further, the size and absorbent capacity of the absorbent core may be varied to accommodate wearers ranging from infants through adults. The absorbent core 9 may comprise one or more absorbent structures as disclosed herein.

Further, the diaper may comprise a front and back waist band and/or a fastening system, typically joined to the waistband, as known in the art. Preferred fastening systems comprise fastening tabs 18 and landing zones 19, wherein the fastening tabs are attached or joined to the back region of the diaper and the landing zones are part of the front region of the diaper. The diaper has also leg cuffs 20 and/or barrier cuffs. Suitable cuffs are described in for example U.S. Pat. No. 3,860,003; U.S. Pat. No. 4,808,178; U.S. Pat. Nos. 4,695,278 and 4,795,454.

Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

Figure 5:
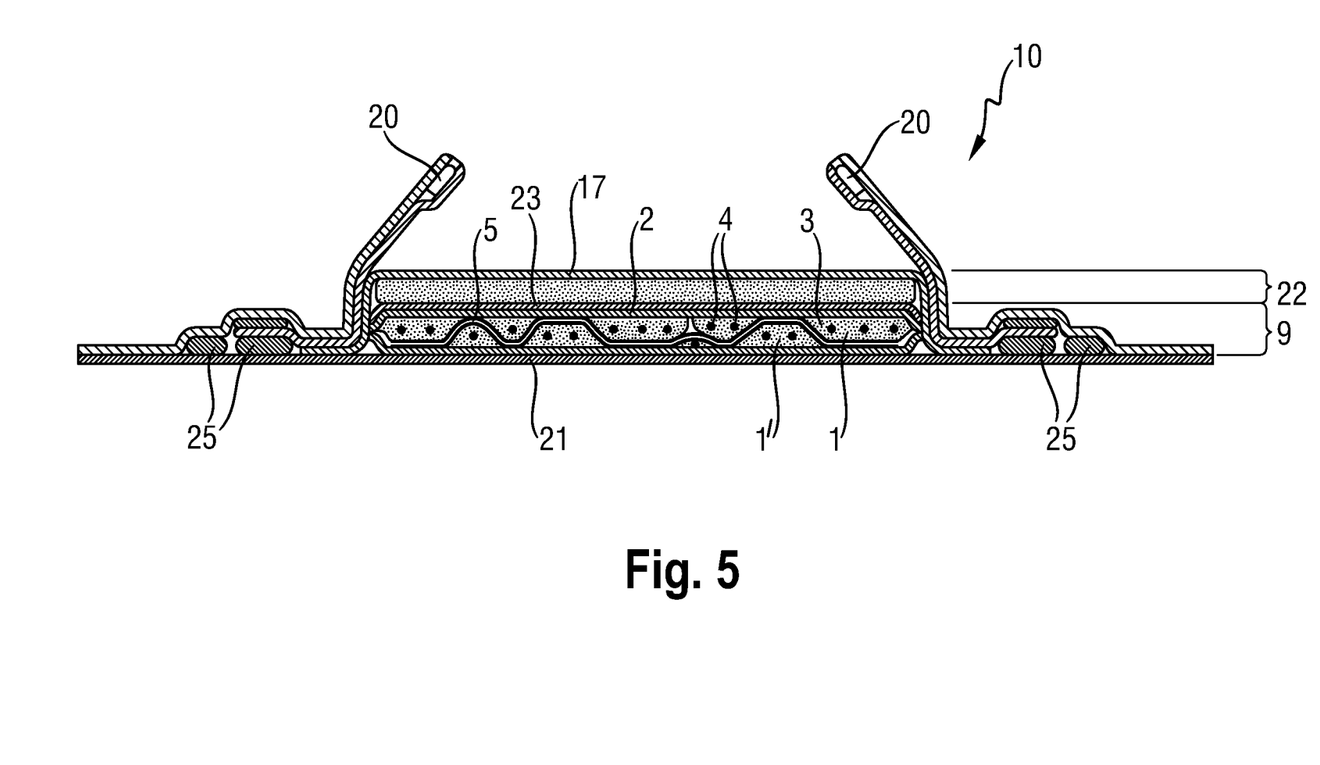
FIG. 5 is a schematic cross-section of the diaper of FIG. 4 taken in the transverse axis A-A'.

FIG. 5 shows a cross section of FIG. 4, taken along the sectional line A-A' of FIG. 4. Starting from the wearer facing side, the diaper may comprise the topsheet 17, the components of the absorbent core 9, of which the absorbent structure 1 and 1' of the present invention, and the backsheet 21. In some embodiment, such as illustrated in FIG. 5 the diaper may also comprise an acquisition system 22 disposed between the liquid permeable topsheet 17 and a wearer facing side of the absorbent core 9, for instance between the cover layer 23 of the core 9 and the topsheet 17. The acquisition system 22 may be in direct contact with the absorbent core 9. The acquisition system may comprise a single layer or multiple layers, such as an upper acquisition layer facing towards the wearer's skin and a lower acquisition layer facing the garment of the wearer. The acquisition system may function to receive a surge of liquid, such as a gush of urine. In other words, the acquisition system may serve as a temporary reservoir for liquid until the absorbent core can absorb the liquid. The acquisition layer can for example comprise fibrous nonwoven materials made by air laying or wet laying of synthetic fibres such as polyethylene (PE), polyethylene terephthalate (PET), or polypropylene (PP), similarly to the cover layer of the absorbent core. Exemplary materials for the fluid acquisition layer could comprise spunbonded or carded nonwoven materials, or airlaid materials such as for example latex bonded or thermal bonded airlaid materials. Basis weights can typically range from about 10 g/m$^2$ to about 60 g/m$^2$, or from about 25 g/m$^2$ to about 40 g/m$^2$. The diapers also comprises elastic members 25.

Figure 6:
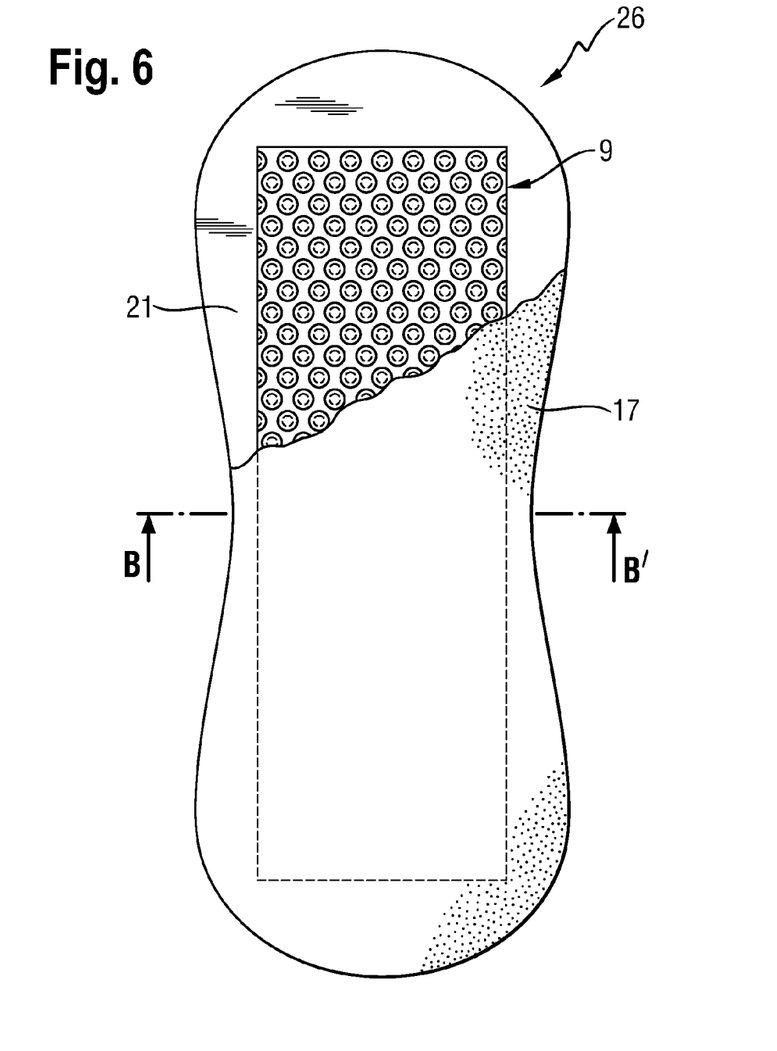
FIG. 6 is a sanitary napkin with portions of some constituent elements cut out in order to show underlying elements.

FIG. 6 illustrates a feminine hygiene product 26 (e.g., sanitary napkin or panty-liner). A feminine hygiene product may comprise a topsheet 17, a backsheet 21, and an absorbent core 9 comprising one or more absorbent structures 1 according to the present invention positioned between the topsheet 17 and the backsheet 21. The size and shape of the absorbent core can be altered to meet absorbent capacity requirements, and to provide comfort to the wearer/user. The backsheet can be any known or otherwise effective backsheet material, provided that the backsheet prevents external leakage of exudates absorbed and contained in the feminine hygiene article. The feminine hygiene product may also comprise wings which may enable attachment to the underwear of the wearer (not illustrated in the figure). The sanitary napkins and/or panty-liners herein may preferably comprise a fastening means comprised by the backsheet and/or by the wings. Preferred are adhesive attachment means that are present on or attached to at least the backsheet.

Figure 7:
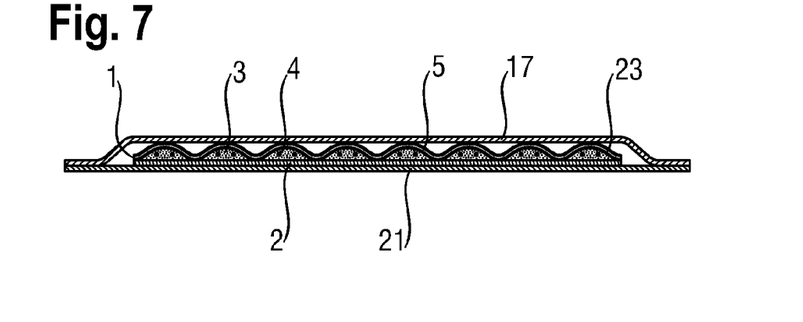
FIG. 7 is a schematic cross-section of the sanitary napkin of FIG. 6 taken in the transverse axis B-B'.

FIG. 7 shows a cross section of FIG. 6, taken along the sectional line B-B' of FIG. 6. Starting from the wearer facing side, the feminine hygiene product comprises the topsheet 17, the components of the absorbent core 9, of which the absorbent structure 1 of the present invention, and the backsheet 21. In some embodiment, such as illustrated in FIG. 6 the absorbent core comprises a cover layer 23.

Absorption Index:

This test serves to determine the impact of a thermoplastic adhesive component on the absorption of absorbent polymer particles within a set time (e.g. 60 sec) in the presence or absence of an oil-scavenger component. The absorption (amount in g/g) is measured over the set time immediately after mixing the components of the sample (i.e. the absorbent polymer particles, the thermoplastic adhesive material and suitably the oil-scavenger component) and measured over the same set time after aging the sample at 40 or 60° C. for 1 week. The test is done as follows:

Preparation of Thermoplastic Adhesive Component Samples

Into a 70 mm diameter aluminum tray, 5 gr of the thermoplastic adhesive material are added. The tray is placed into a 165° C. vented oven for about 1 hour, so that the thermoplastic adhesive material is soft enough to flow. The tray is then removed from the oven and gently tilted from side to side to ensure an even coating of flowable thermoplastic adhesive material across the bottom surface of the tray.

The tray is then cooled to 22° C.±1° C. A 5 gr. thermoplastic adhesive material sample ready for testing is obtained. This procedure is repeated for each of the samples required in the tests.

Determination of the Absorption Index for "Fresh" Sample, "Aged" Sample and "Control" Sample A tray with one of the now cooled thermoplastic adhesive material samples (as prepared above) is placed onto a balance pan and the balance is tared.

0.50 g of the absorbent polymer material sample is mixed with the oil-scavenger component sample (0.5-20 wt %) in a vial to ensure uniform particles distribution throughout the sample.

The contents of the vial are then sprinkled evenly over the entire surface of the thermoplastic adhesive material sample in the tray, ensuring uniform coverage. Then the tray is placed back onto the tared balance pan and the combined weight of the absorbent polymer material sample and oil-scavenger component sample ($W_{dry\ AGM+OS}$) is recorded.

The sample trays thus prepared will be either tested immediately (to get a test value for the "fresh" sample) or after "aging" (i.e. stored 1 week at 40° C. and/or 60° C. in vented oven). After aging, the samples are cooled to 22° C.±1° C. before continuing with the experiment.

Per sample, 6 trays should be prepared to obtain 3 measurements per "fresh" sample type and 3 measurements per "aged" sample type (1 week at 40° C. or 60° C.).

As readily understood, no oil-scavenger component is mixed with the absorbent polymer material when preparing the "fresh" and "aged" control samples.

The tray and a cup with a screen at the bottom are weighed to obtain a combined weight of said tray and cup ($W_{combined}$). The cup is of Plexiglas and has a screen on the bottom. The cup has the following dimensions: 60 mm Internal Diameter, 70 mm Outer Diameter, 60 mm height and the screen is a 100 mesh.

The cup is then placed onto 10 plies of Ahlstrom Grade 989 (4"×4") filter paper. With a dispenser, exactly 20 mL of 0.9% saline solution dyed with 20 ppm FD&C blue #1, is measured and added into the tray, within 3 seconds. Then, the sample is allowed to absorb this saline solution for exactly 60 seconds.

After exactly 60 seconds, the saline solution is poured from the tray into the cup (removing the excess liquid not absorb by the absorbent polymer material but preventing the absorbent polymer material from passing through the screen in the bottom of the cup). The tray is gently tapped against the top of the cup to remove any residual liquid. After exactly 30 seconds of draining, the tray and cup are weighed again ($W_{combined+saline\ absorbed}$).

The weight of the absorbed saline $W_{saline\ absorbed}$ can then be calculated:

$$W_{saline\ absorbed} = W_{combined+saline\ absorbed} - W_{combined}$$

Then the saline absorption in g/g can be calculated:

$$SA(g/g) = W_{saline\ absorbed}(g)/W_{dryAGM+OS}(g)$$

This is repeated twice, to obtain 3 Saline Absorption values, and this is then averaged, to obtain the average Saline Absorption (g/g) of a certain sample ($SA_{sample\ average}$).

This test is performed for each of the "fresh" samples three times in order to obtain the average Saline Absorption values (g/g) per fresh sample ($SA_{fresh\ sample\ average}$).

The test is performed for each of the "aged" samples three times in order to obtain the average Saline Absorption values (g/g) per aged sample ($SA_{aged\ sample\ average}$).

The test is also performed three times per "fresh" control (absorbent polymer material without the oil-scavenger component) and per "aged" control (absorbent polymer material without the oil-scavenger component) to obtain respectively the average Saline Absorption values (g/g) per "fresh" control ($SA_{fresh\ AGM\ average}$) and per "aged" control ($SA_{aged\ AGM\ average}$).

The average amount of saline absorbed by a "fresh" sample $SA_{fresh\ sample\ average}$ may be then compared with the average amount of saline absorbed by an "fresh" control sample $SA_{fresh\ AGM\ average}$ or with the average amount of saline absorbed by an "aged" sample $SA_{aged\ sample\ average}$ of a specific sample.

As well, the average amount of saline absorbed by an "aged" sample aged for 1 week at 40° C. or 60° C., $SA_{aged\ sample\ average}$ can be compared with the average amount of saline absorbed by an "aged" control sample $SA_{aged\ AGM\ average}$ (said aged sample being aged for 1 week at 40 or 60° C., in the manner described above).

The Absorption Index for a sample containing a particular oil-scavenger component can then be determined by:

$$AI_{oilscavenger} = SA_{aged\ sample\ average} / SA_{fresh\ sample\ average}$$

Similarly, the Absorption Index for a control sample (absorbent polymer material without oil-scavenger component) can be determined by:

$$AI_{control} = SA_{aged\ AGM\ average} / SA_{fresh\ AGM\ average}$$

Results of a test performed with different absorbent polymer materials, thermoplastic adhesive materials and oil-scavenger components are summarized in the table below.

| | Absorbent Polymer Material | Thermoplastic Adhesive Material | Oil-Scavenger Component (wt %) | Aging Temperature (° C.) | Absorption Index after 7 days aging |
|---|---|---|---|---|---|
| Control 1 | CP*12[1] | HL 1358[2] | None | 40 | 0.73 |
| # 1 | CP*12 | HL 1358 | Dodecanedioic Acid[3] (20%) | 40 | 0.87 |
| # 2 | CP*12 | HL 1358 | Hexadecanedioic Acid[3] (20%) | 40 | 1.09 |
| # 3 | CP*12 | HL 1358 | 1,2-Dodecanediol[4] (10%) | 40 | 0.75 |
| # 4 | CP*12 | HL 1358 | 1,2-Dodecanediol (20%) | 40 | 0.94 |
| # 5 | CP*12 | HL 1358 | FAM plugs[5] (1%) | 40 | 0.81 |
| # 6 | CP*12 | HL 1358 | FAM plugs (10%) | 40 | 0.80 |
| # 7 | CP*12 | HL 1358 | FAM ground[6] (1%) | 40 | 0.79 |
| # 8 | CP*12 | HL 1358 | FAM ground (10%) | 40 | 0.89 |
| # 9 | CP*12 | HL 1358 | FAM ground (20%) | 40 | 1.01 |
| # 10 | CP*12 | HL 1358 | Crosslinked Polystyrene[7] (10%) | 40 | 1.05 |
| # 11 | CP*12 | HL 1358 | Aerosil 200[8] (0.5%) | 40 | 0.83 |
| # 12 | CP*12 | HL 1358 | Aerosil 200 (1%) | 40 | 0.90 |
| # 13 | CP*12 | HL 1358 | Kaolin[9] (20%) | 40 | 1.07 |
| Control 2 | L597[10] | HL 1358 | None | 40 | 1.11 |
| # 14 | L597 | HL 1358 | 1,2-Dodecanediol (20%) | 40 | 1.30 |
| Control 3 | CP*12 | NW 1151[2] | None | 60 | 0.66 |
| # 15 | CP*12 | NW 1151 | FAM ground (10%) | 60 | 0.72 |
| # 16 | CP*12 | NW 1151 | FAM ground (20%) | 60 | 0.94 |
| # 17 | CP*12 | NW 1151 | Aerosil 200 (1%) | 60 | 0.84 |
| # 18 | CP*12 | NW 1151 | Aerosil 200 (5%) | 60 | 1.01 |
| # 19 | CP*12 | NW 1151 | Kaolin (20%) | 60 | 1.02 |
| Control 4 | L597 | NW 1151 | None | 60 | 0.94 |
| # 20 | L597 | NW 1151 | Hexadecanedioic Acid (20%) | 60 | 1.06 |
| # 21 | L597 | NW 1151 | FAM ground (1%) | 60 | 0.95 |
| # 22 | L597 | NW 1151 | FAM ground (10%) | 60 | 1.08 |

|  | Absorbent Polymer Material | Thermoplastic Adhesive Material | Oil-Scavenger Component (wt %) | Aging Temperature (° C.) | Absorption Index after 7 days aging |
|---|---|---|---|---|---|
| Control 5 | L597 | NW 1151 | None | 40 | 0.92 |
| # 23 | L597 | NW 1151 | 1,2-Dodecanediol (20%) | 40 | 1.03 |

[1]CP*12 is a 2.5% Noveon Permax 200 coated AGM supplied by BASF prepared according to the procedure described herein below.
[2]HL 1358 and NW 1151 are thermoplastic adhesive material supplied by HB Fuller.
[3]Dodecanedioic Acid and Hexadecanedioic Acid are supplied by TCI.
[4]1,2-Dodecanediol (90% purity) is supplied by Aldrich.
[5]FAM is supplied by P&G (FAM-V-028 ~2 mm in size)
[6]FAM is supplied by P&G (FAM-V-028 - Ground ~200-1000 μm).
[7]Divinyl benzene cross-linked styrene polymer is supplied by P&G and prepared according to US application Ser. No. 12/972593.
[8]Aerosil 200 is supplied by Evonik.
[9]Kaolin is supplied by MPSI.
[10]L597 is a NSCL supplied AGM.

Preparation of 2.5% Noveon Permax 200 coated AGM

Absorbent polymer particles ASAP 510 Z (ex. BASF A; sold with a particle size range 150-850 μm) were coated with Permax 200 (Noveon, Brecksville) at an add-on level of 2.5% Permax, and a deagglomeration aid, as follows.

A Wurster coater (available at The Coating Place) was used for the coating step. The Wurster tube was 50 mm in diameter and 150 mm in length, the gap width (distance from base plate) was 15 mm, the Wurster apparatus was conical with a lower diameter of 150 mm expanding to an upper diameter of 300 mm, the carrier gas used was nitrogen having a temperature of 24° C., the gas speed was 3.1 m/s in the Wurster tube and 0.5 m/s in the surrounding annular space.

An aqueous dispersion of absorbent polymer particles (ASAP 510Z) was made and atomized using a nitrogen-driven two-material nozzle, opening diameter 1.2 mm, (from Fa. Schlick (Germany) operated in bottom spray mode, opening diameter 1.2 mm, the nitrogen temperature being 25° C.). The Permax 200 dispersion was sprayed as an 11% by weight aqueous dispersion. The inlet temperature and coating bed temperature was 170° C.

After spraying of the Permax dispersion was finished, 0.5% by weight (of the uncoated absorbent polymer particles) of tricalcium phosphate dispersion was added, as deagglomeration aid, into the coater and fluidized with the coated particles for 5 minutes, to ensure it was present at the particles homogeneously. Then, the coated particles were annealed at 175° C. for 5 min in the coater. Then, the thus coated absorbent polymer particles were sieved, to obtain the 150-500 nm fraction only, which was used in the testing herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure for use in disposable absorbent articles comprising:
   (a) a substrate layer,
   (b) absorbent polymer particles supported by said substrate layer,
   (c) a thermoplastic adhesive material comprising one or more oily substances, said thermoplastic adhesive material immobilizing said absorbent polymer particles on said substrate layer,
   (d) a particulate, single oil-scavenger component contacting said absorbent polymer particles and said thermoplastic adhesive material;
      wherein the oil-scavenger component is a monomer selected from the group consisting of an aliphatic mono- or dihydric alcohol having at least 12 carbon atoms and an aliphatic mono- or dicarboxylic acid having at least 12 carbon atoms;
      wherein the particulate, single oil-scavenger component is deposited exclusively on or beneath the absorbent polymer particles.

2. The absorbent structure according to claim 1 wherein said absorbent structure comprises less than 5% by weight of cellulose.

3. The absorbent structure according to claim 1 or 2 wherein the absorbent polymer particles, thermoplastic adhesive material comprising one or more oily substances and the oil-scavenger component in combination exhibits a ratio $(AI_{oilscavenger}/AI_{control}) > 1$ as measured according to the Absorption Index Method.

4. The absorbent structure according to claim 1 wherein the weight ratio of the absorbent polymer particles to the oil-scavenger component is from 2:1 to 1000:1.

5. The absorbent structure according to claim 1, wherein said absorbent structure further comprises a cover layer covering said absorbent polymeric particles, oil-scavenger component and thermoplastic adhesive material.

6. The absorbent structure according to claim 1, wherein said aliphatic mono- or dihydric alcohol is selected from the group consisting of 1-octadecanol, 1,2-dodecanediol, 1,2-hexadecanediol, 1-tetradecanol, 1,2-tetradecanediol, 1,14-tetradecanediol, 1,2-octadecanediol, and 1,12-octadecanediol.

7. The absorbent structure according to claim 1, wherein said aliphatic mono- or dicarboxylic acid is selected from the group consisting of dodecanoic acid, octadecanoic acid, hexadecanedioic acid, tetradecanoic acid, and tetradecanedioic acid.

8. The absorbent structure according to claim 1, wherein the substrate layer is selected from the group consisting of nonwoven material, foam and film.

9. The absorbent structure according to claim 1, wherein said oil-scavenger component is in particulate form and has an average particle size of from 0.005 μm to 5 mm.

10. A disposable absorbent article comprising an absorbent structure according to claim 1, wherein said disposable absorbent article is selected from the group consisting of diapers, incontinence pads, sanitary napkins and pantyliners.

11. A process for making an absorbent structure according to claim 1 comprising the steps of:
   (a) providing a substrate layer,
   (b) providing absorbent polymer particles,
   (c) providing a thermoplastic adhesive material comprising one or more oily substances,
   (d) providing an oil-scavenger component in particulate form, wherein the oil-scavenger component is a monomer selected from the group consisting of an aliphatic mono- or dihydric alcohol having at least 12 carbon atoms and an aliphatic mono- or dicarboxylic acid having at least 12 carbon atoms, and
   (e) depositing the absorbent polymer particles on the substrate layer, depositing the oil-scavenger particles exclusively on the absorbent polymer particles and depositing the thermoplastic adhesive material on the oil-scavenger particles.

12. The process according to claim 11 further comprising the step of depositing a further thermoplastic adhesive material on the substrate layer prior to step (e).

13. The process according to claim 11 or 12 wherein it further comprises the steps of providing a cover layer and disposing said cover layer over said absorbent polymer particles, oil-scavenger component and thermoplastic adhesive material.

14. The process according to claim 11 comprising the steps of repeating at least once steps (a) to (e) to obtain a further absorbent structure and combining the absorbent structures to obtain an absorbent core comprising several absorbent structures.

* * * * *